United States Patent [19]
Kiehs et al.

[11] 3,962,316
[45] June 8, 1976

[54] CARBAMATE

[75] Inventors: Karl Kiehs, Lampertheim; Rolf Huber, Ludwigshafen; Heinrich Adolphi, Limburgerhof, all of Germany

[73] Assignee: BASF Aktiengesellschaft, Ludwigshafen (Rhine), Germany

[22] Filed: Mar. 17, 1975

[21] Appl. No.: 558,885

Related U.S. Application Data

[63] Continuation-in-part of Ser. No. 371,778, June 20, 1973, abandoned.

[30] Foreign Application Priority Data
June 26, 1972 Germany............................ 2231249

[52] U.S. Cl............................. 260/479 C; 424/300
[51] Int. Cl.² ........................................ C07C 125/06
[58] Field of Search ................................ 260/479 C

[56] References Cited
UNITED STATES PATENTS

| | | |
|---|---|---|
| 3,238,091 | 3/1966 | Bocker................................ 260/479 |
| 3,492,335 | 1/1970 | Gubler................................ 260/479 |
| 3,843,720 | 10/1974 | Nikles................................ 260/479 |
| 3,910,991 | 10/1975 | Nikles............................ 260/479 C |

FOREIGN PATENTS OR APPLICATIONS

| | | |
|---|---|---|
| 801,449 | 12/1973 | Belgium |
| 2,231,249 | 1/1974 | Germany |

*Primary Examiner*—James A. Patten
*Attorney, Agent, or Firm*—Johnston, Keil, Thompson & Shurtleff

[57] ABSTRACT

New and valuable carbamates containing alkoxy groups and a process for controlling pests with these compounds.

4 Claims, No Drawings

CARBAMATE

This application is a continuation-in-part of U.S. patent application Ser. No. 371,778, filed on June 20, 1973, now abandoned.

The present invention relates to new and valuable carbamates; pesticides containing these compounds as active ingredients; and a process for controlling pests with these compounds.

It is known to use 1-naphthyl-N-methylcarbamate and o-isopropoxyphenyl-N-methylcarbamate as insecticides. However, their action is poor.

We have now found that carbamates of the formula

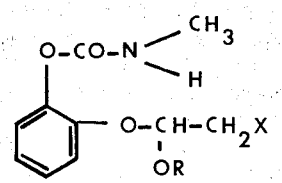

where R denotes methyl or ethyl and X is chlorine, bromine or iodine, have excellent acaricidal and insecticidal properties and are also suitable for combatting ectoparasites and endoparasites in animals. They have a very good action not only on biting and sucking insects but also on mites and ticks. Phytotoxicity is low. The action sets in rapidly and lasts for a long time. For this reason the compounds of the invention may be successfully used in the plant protection sector for combatting injurious sucking and biting insects and Diptera, and for combatting Acarina in the plant protection and veterinary sectors. Of special importance in this connection is the excellent action of the compounds on strains of mites which are resistant to phosphoric esters.

The main members of the group of sucking insects are aphids such as the green peach aphid (*Myzus persicae*) and the bean aphid (*Doralis fabae*); scales, such as *Aspidiotus hederea*, *Lecanium hesperidum*, *Pseudococcus maritimus*; Thysanoptera, such as *Hercinothrips femoralis*; and bugs, such as *Piesma quadrata* and the bed bug (*Cimex lectularius*).

The main members of the group of biting insects are caterpillars, such as *Plutella maculipennis* and *Lymantria dispar*; beetles, such as the granary weevil (*Sitophilus granarius*), Colorado potato beetle (*Leptinotarsa Decembineata*), and also types living in the soil, e.g., wireworms (*Agriotes* sp.) and cockchafer (*Melolontha melolontha*); bugs, such as the croton bug (*Blattela germanica*); Orthoptera, such as the housecricket (*Gryllus domesticus*); termites, such as Reticulitermes; and Hymenoptera, such as ants.

The Diptera include in particular the flies, e.g. fruit fly (*Drosophila melanogaster*); Mediterranean fruit fly (*Ceratitis capitata*); housefly (*Musca domestica*); gnats such as the yellow fever mosquito (*Aedes aegypti*) and *Culex pipilus*; bluebottles, such as *Lucilia sericata*; and blowflies (*Chrysomya chloropyga*).

Of the mites, the following are of particular importance: Tetranychidae, such as the red spider mite (*Tetranychus urticae*) and *Paratetranychus pilosus*; gall mites, such as the currant mite (*Eriophyes ribis*) and Tarsonemidae, such as *Tarsonemus pallidus*; ticks, e.g. *Boophilus microplus*, and itch mites.

Application of the compounds is by conventional methods, e.g., spraying, atomizing, fuming, broadcasting, etc.

The new carbamates may be prepared for instance by reacting a phenol of the formula II

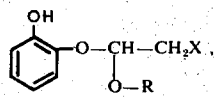

where R and X have the above meanings, with methyl isocyanate or N-methylcarbamyl chloride. The phenol may also be converted into the new carbamates via the chloroformate by reaction with methylamine. Phenols of the formula II may be prepared in accordance with conventional methods for the synthesis of acetals or ketals, for instance pyrocatechol may be reacted in a molar ratio of 1:1 with a suitably substituted α-halo ether, trans-acetalization may sometimes be useful, in which case the alcohol component of the acetal or ketal used should contain a low number of carbon atoms, expediently 1 to 4 in order for it to be easily removed by distillation from the reaction vessel; the equilibrium is shifted in the direction of the desired products of the formula II.

Further, carbamates of the formula III

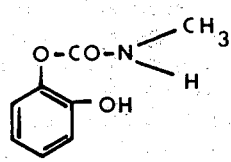

may be reacted to the new carbamates with α-halo ethers of the formula IV

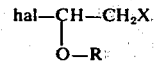

where R and X have the above meanings and hal denotes chloro or bromo, with the aid of suitable bases (e.g. alkali metal hydroxides, tertiary amines) in indifferent solvents (e.g. tetrahydrofuran, dioxane, benzene, toluene, xylene, diethylene glycol dimethyl ether). The α-halo ethers required for this route are prepared by conventional methods.

Carbamates of the formula III may, by acid catalysis, also be reacted to the new carbamates with acetals or ketals of the formula V

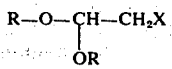

where R and X have the above meanings, by partial transacetalization or trans-ketalization, one alcohol of the formula ROH being distilled off.

The number of carbon atoms in the alcohols ROH is 1 or 2. The alcohols may be easily removed from the reaction mixture by distillation, thus shifting the reaction equilibrium in the desired direction.

Appropriately substituted vinyl ethers are also suitable for the production of the new carbamates; carbamates of the formula III are reacted in conventional manner by acid catalysis with the vinyl ethers which in turn have been prepared by known methods. The route selected depends on the availability of the alkylating agent. The examples below demonstrate the various production methods.

EXAMPLE 1 a. Over a period of 1 hour and at 20° to 30°C, 129 parts (by weight) of 1,2-dichloroethyl methyl ether is dripped into a solution of 110 parts of pyrocatechol and 101 parts of triethylamine in 500 parts of tetrahydrofuran. The mixture is then stirred for approx. 6 hours. The amine hydrochloride is subsequently filtered off, the solvent distilled off, and the residue purified with chloroform/water. After the chloroform has been removed by distillation there is obtained 196 parts of o-(α-methoxy-β-chloro)-ethoxyphenol; $n_D^{25}$ = 1.5215.

At about 25°C, a few drops of triethylamine and subsequently 6.3 parts of methyl isocyanate are added to a solution of 25 parts of tetrahydrofuran in 20.2 parts of o-(α-methoxy-β-chloro)-ethoxyphenol. The end product is formed in a weakly exothermic reaction. After stirring for 2 hours at 50°C the volatiles are distilled off at 40° to 50°C under a water jet vacuum. After recrystallization from ether there is obtained 20.5 parts of o-(α-methoxy-β-chloro)-ethoxyphenyl-N-methylcarbamate as colorless crystals; m.p.: 70°C.

b. A mixture of 8.3 parts of pyrocatechol mono-N-methylcarbamate, 5.1 parts of triethylamine and 7.1 parts of 1,2-dichloroethyl methyl ether in 75 parts of toluene is heated for about 5 hours at 100° to 110°C. After the volatiles have been distilled off in vacuo the residue is taken up in chloroform, filtered and washed with 0.5% (by weight) aqueous sodium bicarbonate solution. The residue remaining after the chloroform has been distilled off may be recrystallized from a mixture of ether and ligroin. Yield: 9.7 parts of o-(α-methoxy-β-chloro)-ethoxyphenyl-N-methylcarbamate; m.p.: 69° to 71°C.

EXAMPLE 2

At room temperature, about 0.5 part of boron trifluoride etherate is added to a solution of 8.3 parts of pyrocatechol mono-N-methylcarbamate and 5.9 parts of 2-chloroethyl vinyl ether in 25 parts of tetrahydrofuran. The mixture is then stirred for 1 hour at room temperature and for about 3 hours at the boiling temperature. After the volatiles have been distilled off there is obtained 12.4 parts of o-(α-2-chloroethoxy)-ethoxyphenyl-N-methylcarbamate as an oil; $n_D^{25}$ = 1.5211.

Examples of other new carbamates are:

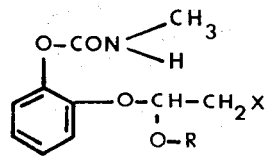

| R | X | m.p. ($n_D^{25}$) |
|---|---|---|
| $C_2H_5$ | Cl | (1.5125) |
| $CH_3$ | Br | 70° to 72°C |
| $CH_3$ | I | (1.5465) |

The agents according to the invention may be used as solutions, emulsions, suspensions or dusts. The form of application depends entirely on the purpose for which the agents are being used; in any case it should ensure a fine distribution of the active ingredient.

For the preparation of solutions to be sprayed direct, the solution in water is suitable. However, hydrocarbons having boiling points higher than 150°C, e.g. tetrahydronaphthalene or alkylated naphthalenes, or organic liquids having boiling points higher than 150°C and having one or more than one functional group, e.g. the keto group, the ether group, the ester group or the amide group, this group or these groups being attached as substituent(s) to a hydrocarbon chain or being a component of a heterocyclic ring, may also be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts or granules may be prepared by mixing or grinding the active ingredients with a solid carrier, e.g., kieselguhr, talc, clay or fertilizers.

EXAMPLE 3

90 parts by weight of the compound of Example 1 is mixed with 10 parts by weight of N-methyl-α-pyrrolidone. A mixture is obtained which is suitable for application in the form of very fine drops.

EXAMPLE 4

20 parts by weight of the compound of Example 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 5

20 parts by weight of the compound of Example 1 is dissolved in a mixture consisting of 40 parts by weight of cyclohexanone, 30 parts by weight of isobutanol, 20 parts by weight of the adduct of 7 moles of ethylene oxide to 1 'mole of isooctylphenol, and 10 parts by weight of the adduct of 40 moles of ethylene oxide to 1 mole of caster oil. By pouring the solution into 100,000 parts by weight of water and uniformly distributing it therein, an aqueous dispersion is obtained containing 0.02% by weight of the active ingredient.

EXAMPLE 6

20 parts by weight of the compound of Example 1 is dissolved in a mixture consisting of 25 parts by weight of cyclohexanol, 65 parts by weight of a mineral oil fraction having a boiling point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of the compound of Example 1 is well mixed with 3 parts by weight of the sodium salt of diisobutyl-naphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 8

3 parts by weight of the compound of Example 2 is intimately mixed with 97 parts by weight of particulate kaolin. A dust is obtained containing 3% by weight of the active ingredient.

EXAMPLE 9

30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

For the following experiments the following active ingredients were used:

1. 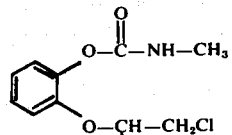 (according to the invention)

2. 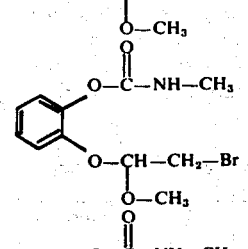 (according to the invention)

6. 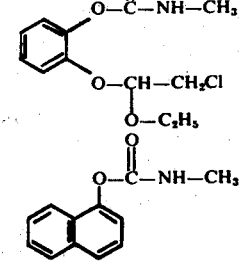 (according to the invention)

I 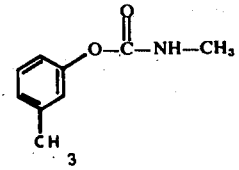 (comparative agent)

II 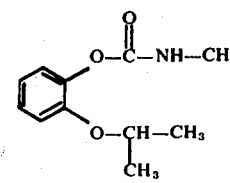 (comparative agent)

III 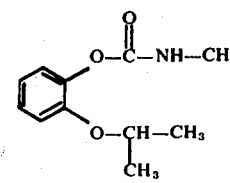 (comparative agent)

IV 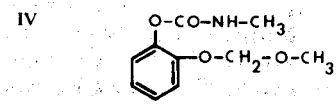

EXAMPLE 10

1 mm³ of an acetonic solution of the active ingredients is applied to the ventral abdomen of houseflies (*Musca domestica*) under slight $CO_2$ narcosis.

The $LD_{50}$ is calculated from the mortality rate of the flies after 4 hours.

| Active ingredient | $LD_{50}$ | | |
|---|---|---|---|
| 1 | 0.41 | γ/fly | |
| 2 | 0.3 | γ/fly | |
| I | 10.0 | γ/fly | ineffective |
| II | 10.0 | γ/fly | ineffective |
| III | 1.5 | γ/fly | |

EXAMPLE 11

Adult oriental cockroaches (*Blatta orientalis*) are placed in 1 liter glass beakers whose inner surfaces have been treated with acetonic solutions of the active ingredients. The action is determined after 48 hours.

| Active ingredient | Amount of active ingredient in mg/breaker | Mortality |
|---|---|---|
| 1 | 0.2 | 100% |
| II | 0.5 | 100% |
| IV | 0.1 | 100% |

-continued
(comparative agent)

-continued

| Active ingredient | Amount of active ingredient in mg/breaker | Mortality |
|---|---|---|
| 1 | 0.05 | 100% |

EXAMPLE 12

Contact action and effect of ingested food on caterpillars of the cabbage moth (*Plutella maculipennis*). Young cabbage leaves are dipped for 3 seconds into aqueous emulsions of the active ingredients. After they have dried they are put into Petri dishes and caterpillars of the cabbage moth are placed on them.

| Active ingredient | Amount of ingredient in aqueous emulsion in % by weight | Mortality |
|---|---|---|
| 1 | 0.1 | 100% |
| II | 0.1 | ineffective |
| III | 0.1 | ineffective |
| IV | 0.1 | ineffective |
| 1 | 0.05 | 100% |
| 6 | 0.02 | 100% |

We claim:
1. o-(α-methoxy-β-chloro)-ethoxyphenyl-N-methyl-carbamate.
2. o-(α-ethoxy-β-chloro)-ethoxyphenyl-N-methyl-carbamate.
3. o-(α-methoxy-β-bromo)-ethoxyphenyl-N-methyl-carbamate.
4. o-(α-methoxy-β-iodo)-ethoxyphenyl-N-methyl-carbamate.

* * * * *